US006266831B1

(12) United States Patent
Heimbrock

(10) Patent No.: US 6,266,831 B1
(45) Date of Patent: Jul. 31, 2001

(54) STORABLE TRAUMA BOARD SUPPORT

(75) Inventor: Richard H. Heimbrock, Cincinnati, OH (US)

(73) Assignee: Hill-Rom, Inc., Batesville, IN (US)

( * ) Notice: Subject to any disclaimer, the term of this patent is extended or adjusted under 35 U.S.C. 154(b) by 0 days.

(21) Appl. No.: 09/298,793

(22) Filed: Apr. 23, 1999

(51) Int. Cl.[7] ................................ A61G 1/04; A61B 6/04

(52) U.S. Cl. ........................... 5/601; 5/507.1; 248/231.61

(58) Field of Search ......................... 5/601, 503.1, 504.1, 5/505.1, 506.1, 507.1, 658; 403/234, 256, 398; 248/121, 122.1, 200, 205.1, 214, 215, 218.4, 226.11, 227.1, 227.4, 228.6, 229.1, 230.6, 231.61

(56) References Cited

U.S. PATENT DOCUMENTS

| | | | | |
|---|---|---|---|---|
| 137,828 | | 4/1873 | Cosby . | |
| 325,993 | | 9/1885 | Underhill . | |
| 803,619 | | 11/1905 | McMahan . | |
| 876,041 | * | 1/1908 | Crosno | 248/231.61 X |
| 1,256,498 | * | 2/1918 | Baker | 248/231.61 X |
| 1,639,801 | | 8/1927 | Heise . | |
| 1,719,614 | * | 7/1929 | McIntosh | 5/507.1 X |
| 1,797,847 | * | 3/1931 | Vandagriff | 5/507.1 X |
| 1,862,237 | * | 6/1932 | Pepler | 5/507.1 X |
| 1,905,887 | | 4/1933 | Berns . | |
| 2,193,647 | * | 3/1940 | Rush et al. | 5/507.1 X |
| 2,483,920 | * | 10/1949 | McLean et al. | 5/507.1 X |
| 2,605,155 | * | 7/1952 | Lewis | 5/507.1 X |
| 2,678,792 | * | 5/1954 | Gallion et al. | 248/226.11 |
| 2,703,265 | * | 3/1955 | Wolfe | 248/214 |
| 3,215,834 | | 11/1965 | Tayman . | |
| 3,530,515 | * | 9/1970 | Jacoby | 5/505.1 |
| 3,840,221 | | 10/1974 | Hogan . | |
| 4,019,772 | | 4/1977 | Lee . | |
| 4,103,170 | | 7/1978 | Spradlin . | |
| 4,169,591 | * | 10/1979 | Douglas | 5/658 X |
| 4,873,710 | | 10/1989 | Lotman . | |
| 4,926,457 | | 5/1990 | Poehner et al. . | |
| 4,947,418 | | 8/1990 | Barr et al. . | |
| 5,127,034 | | 6/1992 | Wright . | |
| 5,166,968 | | 11/1992 | Morse . | |
| 5,255,303 | | 10/1993 | DiMaio et al. . | |
| 5,263,673 | * | 11/1993 | Yang | 5/503.1 X |
| 5,287,577 | | 2/1994 | Bremer et al. . | |
| 5,375,276 | | 12/1994 | Nelson et al. . | |
| 5,422,928 | * | 6/1995 | Payne | 378/177 |
| 5,473,784 | | 12/1995 | Nixon et al. . | |
| 5,806,111 | | 9/1998 | Heimbrock et al. . | |
| 5,996,149 | * | 12/1999 | Heimbrock et al. | 5/601 |
| 6,095,683 | * | 8/2000 | Heimbrock et al. | 378/177 |

FOREIGN PATENT DOCUMENTS

| | | | | |
|---|---|---|---|---|
| 195597 | * | 2/1958 | (AT) | 5/507.1 |
| 3515808 A1 | | 6/1986 | (DE) . | |

OTHER PUBLICATIONS

PCT International Search Reported dated Jul. 19, 2000.

* cited by examiner

*Primary Examiner*—Terry Lee Melius
*Assistant Examiner*—Robert G. Santos
(74) *Attorney, Agent, or Firm*—Barnes & Thornburg

(57) ABSTRACT

In an illustrated embodiment of the present invention, a plurality of trauma board supports are movably coupled to a stretcher for motion between a first position away from a patient support surface of the stretcher and a second position above the patient support surface for releasably supporting a trauma board thereon in a substantially parallel, spaced-apart relation to the patient support surface at a distance sufficient to allow positioning of an x-ray cassette between the trauma board and the patient support surface.

16 Claims, 3 Drawing Sheets

STORABLE TRAUMA BOARD SUPPORT

BACKGROUND AND SUMMARY OF THE INVENTION

This invention generally relates to hospital trauma stretchers, and particularly to trauma stretchers suitable for use with radiolucent trauma boards used for radiography. More particularly, this invention generally relates to trauma stretchers suitable for use with radiolucent trauma boards used for transporting injured patients.

Trauma boards for supporting injured persons during transport to medical facility are currently in widespread use. Injured persons are usually strapped to a trauma board at the site of an accident, the trauma board is, in turn, supported on an ambulance cot, the injured person is driven to a medical facility in an ambulance, and the trauma board and patient are transferred from the ambulance cot to a trauma stretcher which is then wheeled into an emergency department of the medical facility. The injured person remains on the trauma board until all x-rays that need to be taken are taken and the person is cleared of spinal injury.

These trauma boards are generally elongated, flat and rectangular in configuration, and are provided with handhold slots along their periphery into which the paramedics insert their hands to lift and carry the injured person. The trauma boards are typically made from radiolucent materials to assist with taking of x-rays without having to move the patient to and from the trauma board. In addition, it is desirable to take all the x-rays while keeping the patient on a trauma board supported on a trauma stretcher.

In an illustrated embodiment of the present invention, a plurality of trauma board supports are movably coupled for motion between a first position away from a patient support surface and a second position above the patient support surface for releasably supporting a radiolucent trauma board thereon in a substantially parallel, spaced-apart relation to the patient support surface to allow positioning of an x-ray cassette between the trauma board and patient support surface.

In another illustrated embodiment, a pair of frame members are coupled to the opposing sides of a stretcher generally below the patient support surface. A plurality of support sockets, coupled to the frame members, pivotally support a like plurality of trauma board supports for motion between a first position away from the support surface and a second position above and overlying the patient support surface for supporting a trauma board.

In a further embodiment, the trauma board support includes a first portion having a first end pivotally coupled to the support socket and a second end coupled to a second portion extending away from the second end transversely to the first portion for removably supporting a trauma board over the patient support surface. The first portion extends generally vertically and the second portion extends generally horizontally over the patient support surface when the trauma board support is in the second position.

In still another embodiment of the present invention, the first end of the first portion of the trauma board support includes an elongated pin-receiving slot configured for slidably receiving a pivot pin secured to the support socket. To move a trauma board support to a second generally vertical up position and lock it in place, the first portion of the trauma board support is pivoted up about the pivot pin from a first out-of-the-way down position to the second generally vertical up position, and slid downwardly into the support socket to lock the trauma board support in its second generally vertical up position. To return the trauma board support to its first out-of-the-way down position, the first portion of the trauma board support is lifted upwardly to release the lock, and pivoted downwardly about the pivot pin from the generally second generally vertical up position.

In this embodiment, the trauma board support includes an upwardly-protruding portion configured for reception in a cutout in the trauma board for holding the trauma board in place when supported on the trauma board supports.

In a further embodiment, the second portion of the trauma board support can telescope in and out along its length dimension to accommodate different width trauma boards.

In still further embodiment, the support sockets are configured to move lengthwise along the frame members of the stretcher to accommodate different length trauma boards.

In this embodiment, the trauma board support is configured to be moved adjacent to a corner of the patient support surface and pivoted down to its first out-of-the-way down position generally below the patient support surface.

In still another embodiment of the present invention, a trauma board support is pivotally coupled to at least one end of the stretcher, either a head end or a foot end. The trauma board support includes a first portion having a first end pivotally coupled to the at least one end of the stretcher generally below the patient support surface and a second end coupled to a second portion extending away from the second end transversely to the first portion for removably supporting a trauma board over the patient support surface. The first portion extends generally vertically and the second portion extends generally horizontally over the patient support surface when the trauma board support is in the second position.

In this embodiment, the first portion of the trauma board support includes a further portion extending away from the first end transversely to the first portion such that the first portion, the second portion and the further portion generally form a C-shaped configuration. The distal end of the further portion is pivotally coupled to the at least one end of the stretcher generally below the patient support surface.

Illustratively, the trauma board support is disposed under the at least one end of the stretcher generally below the patient support surface when the trauma board support is in the first out-of-the-way down position.

In an alternative embodiment of the present invention, a headboard is coupled to one end of the stretcher. A flip-down panel is pivotally coupled to the headboard for movement between a first position away from the patient support surface and a second position above the patient support surface for removably supporting a trauma board thereon in a substantially parallel, spaced-apart relation to the patient support surface to allow positioning of an x-ray cassette between the trauma board and the patient support surface. In this embodiment, the flip-down panel serves a dual purpose. In addition to providing support to the trauma board when flipped down, it provides a table surface for use by a patient or a caregiver.

In a further alternative embodiment of the present invention, a footboard is coupled to one end of the stretcher. A flip-down panel is pivotally coupled to the footboard for movement between a first position away from the patient support surface and a second position above the patient support surface for removably supporting the trauma board thereon in a substantially parallel spaced-apart relation to the patient support surface to allow positioning of an x-ray cassette between the trauma board and the patient support surface. In this embodiment, the flip-down panel also serves a dual purpose. In addition to providing support to the trauma board when flipped down, it provides a table surface for use by a patient or a care giver.

Additional features of the present invention will become apparent to those skilled in the art upon a consideration of the following detailed description of preferred embodiments exemplifying the best mode of carrying out the invention as presently perceived.

BRIEF DESCRIPTION OF THE DRAWINGS

The detailed description particularly refers to the accompanying figures in which.

DETAILED DESCRIPTION OF THE DRAWINGS

The present invention will be described primarily as an accessory or attachment to a trauma stretcher, but it will be understood that the same may be used as an accessory or attachment to a regular hospital stretcher or a surgical operating table or a hospital bed.

Figure 1:
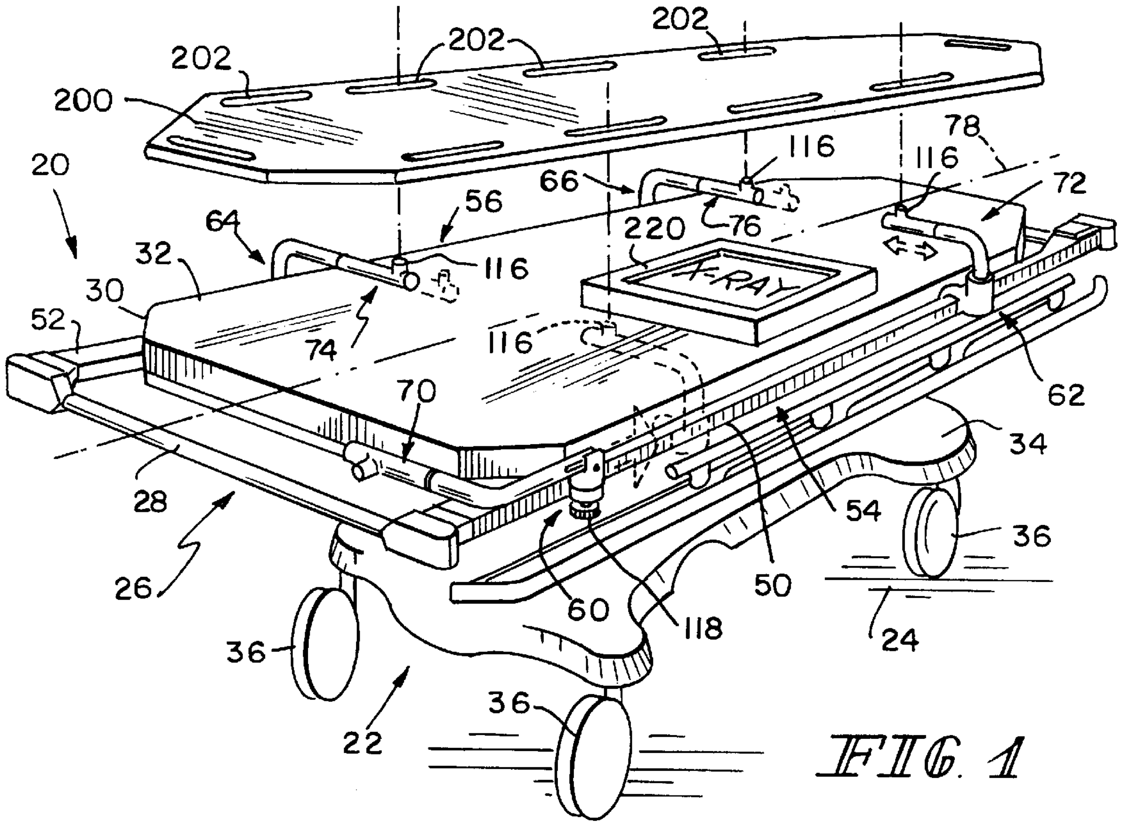
FIG. 1 is a perspective view showing a hospital trauma stretcher including a pair of frame members coupled to the opposing sides of the stretcher generally below a patient support surface, each frame member slidably supporting two support sockets, each support socket pivotally supporting a trauma board support for motion between a first position away from the patient support surface and a second position above the patient support surface for supporting a radiolucent trauma board above the patient support surface in accordance with the present invention, each backboard support having an upwardly-protruding portion for reception in a peripheral cutout in the backboard, an x-ray cassette is shown supported on a mattress between the trauma board and the patient support surface.
Figure 2:
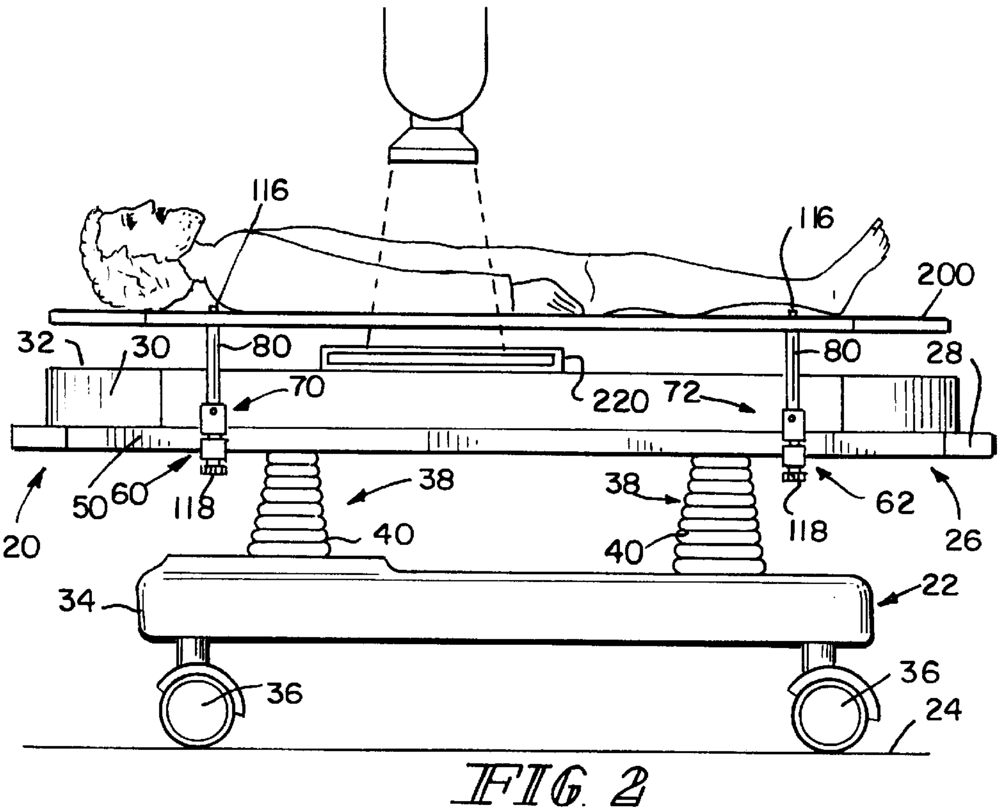
FIG. 2 is a side elevation view of the FIG. 1 trauma stretcher showing a patient resting on a radiolucent trauma board, which, in turn, is supported by the pivotable trauma board supports above the patient support surface, and further showing an x-ray cassette slid into the space between the trauma board and the mattress located on a patient support deck.

As shown in FIGS. 1 and 2, a trauma stretcher 20 includes a base frame 22 supported on a floor 24, an intermediate frame 26 movably mounted to the base frame 22 by high/low mechanisms 38, and an articulatable patient support deck 28 supported on the intermediate frame 26. The patient support deck 28 may include longitudinally spaced-apart back, seat, leg and foot sections (not shown), which are hingedly coupled to each other in seriatim. The seat section is typically coupled to the intermediate frame 26. The back, leg and foot sections are coupled to the intermediate frame 26 for relative motion with respect to each other and the seat section. A mattress 30 is supported on the patient support deck 28. The mattress 30 has an upwardly-facing patient support surface 32 upon which a patient can rest.

The base frame 22 is covered by a protective shroud 34 to shield various mechanisms mounted on the base frame from view and to prevent foreign objects from being inadvertently inserted therein. Relatively large casters 36, mounted at each corner of the base frame 22, extend downwardly therefrom to engage the floor 24. The intermediate frame 26 is supported above the base frame 22 by a pair of longitudinally spaced-apart high/low mechanisms 38, well-known to those skilled in the art. The high/low mechanisms 38 are covered by a protective boot 40 to shield them from view and to prevent foreign objects from being inadvertently inserted therein. The stretcher 20 includes a plurality of foot pedals (not shown) for activating the high/low mechanisms 38 to raise, lower or tilt the intermediate frame 26 and the patient-support deck 28 with respect to the floor 24. The stretcher 20 includes a conventional brake and steer mechanism (not shown). Many of the above mechanisms are described in the U.S. Pat. No. 5,806,111, assigned to the same assignee as the present invention, which is incorporated by reference herein.

The patient support deck 28 of the stretcher 20 includes a pair of frame members 50 and 52 coupled to opposing lengthwise sides 54 and 56 of the intermediate frame 26 for movably supporting a plurality of support sockets 60, 62, 64 and 66. Two support sockets 60, 62 are coupled to the frame member 50, and two support sockets 64, 66 are coupled to the other frame member 52. The plurality of support sockets 60, 62, 64 and 66 pivotally support a like plurality of trauma board supports 70, 72, 74 and 76 for motion between a first position away from the patient support surface 32 and a second position above the patient support surface 32 for removably supporting an x-ray penetrable trauma board 200 thereon in a substantially parallel, spaced-apart relation to the patient support surface 32 to allow positioning of an x-ray cassette 220 between the trauma board 200 and the mattress 30 supported on the patient support deck 28. In FIG. 1, the trauma board support 70 is shown in the first out-of-the-way down position in solid lines, and further shown in the second generally vertical up position in phantom lines. It will be noted that this arrangement provides the ability to hang the x-ray cassette 220 partially out from under the trauma board 200 and also the ability to place the x-ray cassette 220 at an angle to a longitudinal axis 78 of the patient support deck 28, if desired.

The radiolucent trauma board 200 includes a plurality of handhold cutouts 202 around its perimeter into which the paramedics insert their hands to lift and carry the injured person. The radiolucent trauma board 200 may be formed from any suitable rigid, light-weight, high-strength materials or composites, such as various plastics.

Since all four support sockets 60–66 are identical, only one support socket 60 will be described. The description of other support sockets 62–66 is similar. Likewise, only one trauma board support 70 will be described. The description of other trauma board supports 72–76 is similar.

Figures 3, 4:
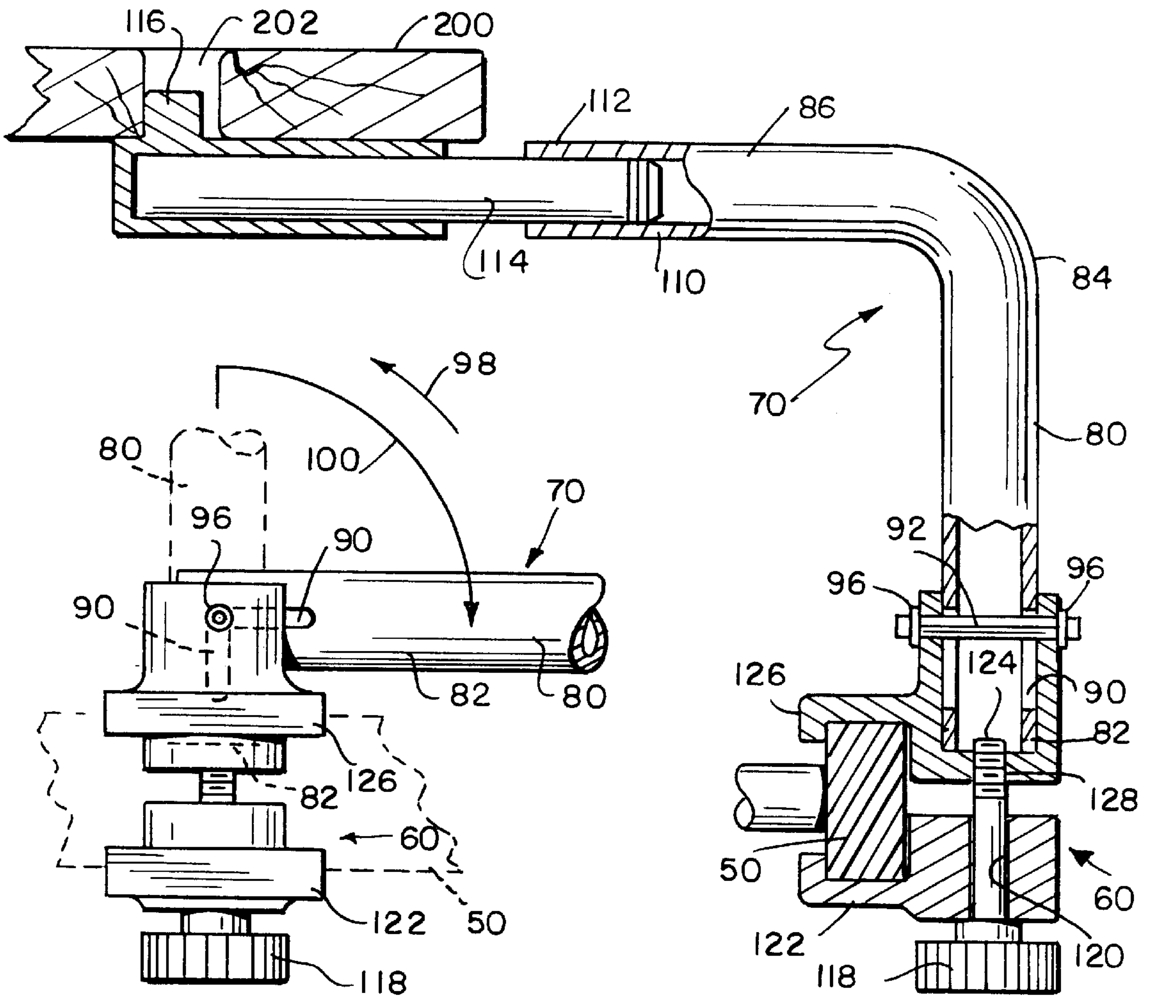
FIG. 3 is a cross-sectional view showing a support socket coupled to a frame member, a trauma board support pivotally coupled to the support socket about a pivot pin extending perpendicularly to a longitudinal axis of the patient support deck and a radiolucent trauma board supported on the trauma board support, the trauma board support including an upwardly-facing locating stud configured for reception in a peripheral cutout in the trauma board for holding the trauma board in place.
FIG. 4 is a view showing additional details of the pivotal coupling of the trauma board support to the support socket, and a mechanism for locking the trauma board support to the support socket, one end of the trauma board support is shown having an elongated pin-receiving slot configured for slidably receiving a perpendicularly-extending pivot pin secured to the support socket, the pivot pin being held in place by two retaining washers attached to its ends.

As shown in FIGS. 3 and 4, the trauma board support 70 includes a first portion 80 having a first end 82 pivotally coupled the support socket 60 and a second end 84 coupled to a second portion 86 extending away from the second end 84 transversely to the first portion 80 for removably supporting the trauma board 200 over the patient support surface 32. The first portion 80 extends generally vertically and the second portion 86 extends generally horizontally over the patient support surface 32 when the trauma board support 70 is in the second position.

The first end 82 of the first portion 80 of the trauma board support 70 includes a pin-receiving slot 90 configured for slidably receiving a pivot pin 92 therein substantially at a 90° angle to the longitudinal axis 78 of the patient support deck 28. The two ends of the pivot pin 92 are supported by the support socket 60, and held in place by two retaining washers 96. To move the trauma board support 70 to its second generally vertical up position and lock it in place, the first portion 80 of the trauma board support 70 is pivoted about the pivot pin 92 from the first generally horizontal down position (as shown in solid lines in FIGS. 1 and 4) to the second generally vertical up position (as shown in phantom lines in FIGS. 1 and 4) in a direction 98, and slid downwardly into the support socket 60 to lock the first portion 80 of the trauma board support 70 in its vertical up position (as shown in FIG. 3). To return the trauma board support 70 to its first out-of-the-way down position, the first portion 80 of the trauma board support 70 is lifted upwardly to release the lock, and pivoted downwardly about the pivot pin 92 from the generally vertical up position (as shown in phantom lines in FIGS. 1 and 4) to the generally horizontal down position (as shown in solid lines in FIGS. 1 and 4) in a direction 100.

As shown in FIG. 3, the distal end 110 of the second portion 86 of the trauma board support 70 includes a tubular portion 112 configured for reciprocably receiving a plunger rod 114, which can telescope in and out of the tubular portion 112 along its length dimension. The plunger rod 114 of the trauma board support 70 includes a portion, such as an upwardly-facing locating stud 116, which is configured for engagement with the trauma board, such as a handhold cutout 202 in the trauma board 200, for holding the trauma board 200 in place. All four trauma board supports 70–76 and the corresponding telescopic plunger rods 114 are padded with a spongy coating, and then overcoated with a tough outer layer to prevent tearing.

The telescopic plunger rods 114 provide the ability for accommodating different width trauma boards. Additionally, the support socket 60 is configured to move lengthwise along the frame members 50 and 52 of the stretcher 20 to provide the ability for accommodating different length trauma boards. As shown in FIGS. 3 and 4, a thumb screw 118 is received by an oversized opening 120 in the lower half 122 of the support socket 60. The distal end 124 of the thumb screw 118 engages a threaded opening 128 in the upper half 126 of each support socket 60 so that rotation of the thumb screw 118 draws the two halves of the support socket 60 together to clamp a frame member between the two halves of the support socket 60.

When not needed, the trauma board supports 70–76 are configured to be moved adjacent to a respective one of the four corners of the patient support deck 28, and pivoted down to their out-of-the-way down position generally below the patient support deck. In FIG. 1, the trauma board support 70 is shown in its out-of-the-way down position.

Figure 5:
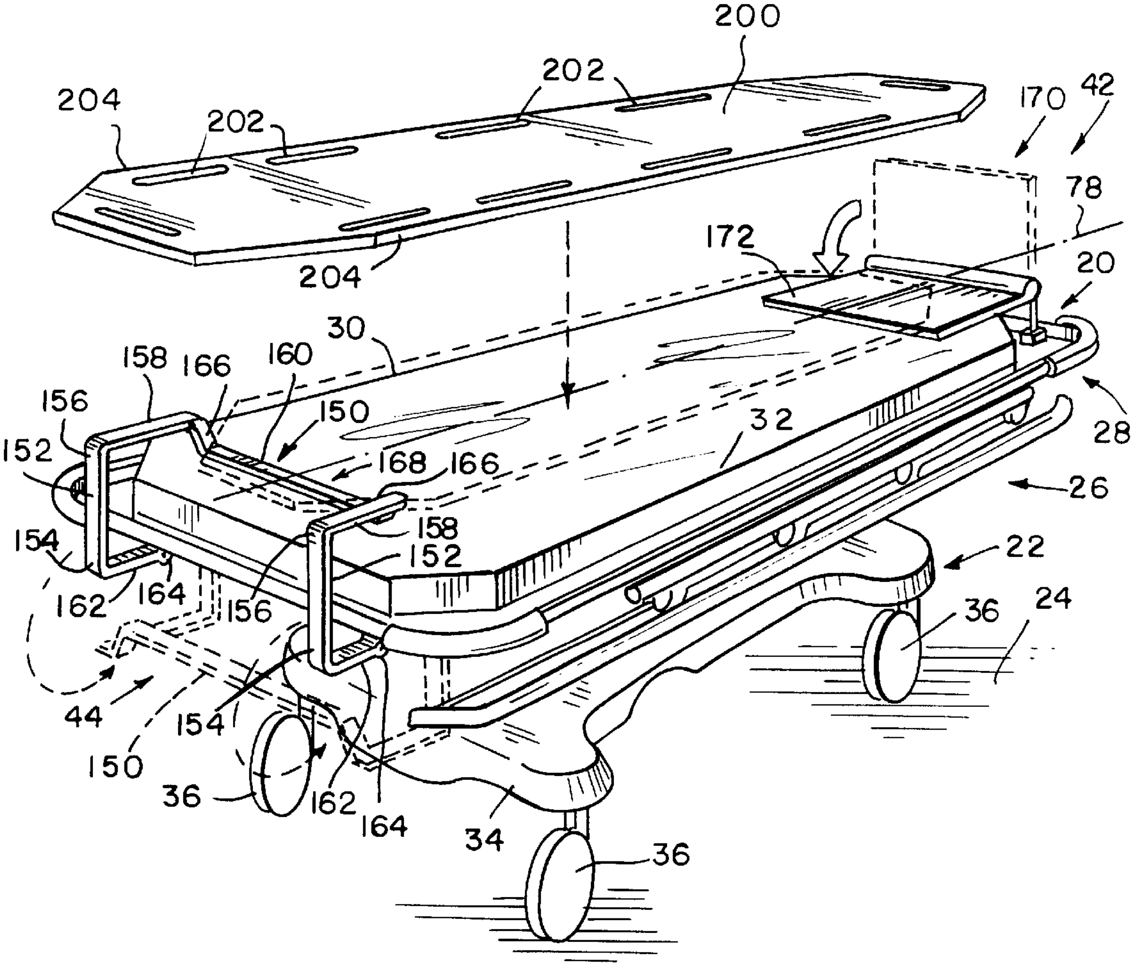
FIG. 5 is a view showing alternate configurations of the trauma board supports, as shown therein the trauma board supports are coupled to the ends of the stretcher, instead of to the sides.

Another embodiment of the present invention is shown in FIG. 5. As shown therein, a trauma board support 150 is pivotally coupled to a foot end 44 of the stretcher 20 for motion between an out-of-the-way down position away from the patient support deck (shown in phantom lines) and a second position above the patient support surface 32 (shown in solid lines) for removably supporting a radiolucent trauma board 200 thereon in a substantially parallel, spaced-apart relation to the patient support surface 32 to allow positioning of an x-ray cassette 220 between the trauma board 200 and a mattress 30 supported on the patient support deck 28.

Although the trauma board support 150 is pivotally coupled to a foot end 44 of the stretcher 20, it may as well be coupled instead to a head end 42 of the stretcher. Also, it will be understood that such trauma board supports may be provided at both ends of the stretcher 20, instead of only at one end of the stretcher 20.

As shown in FIG. 5, the trauma board support 150 includes a pair of laterally spaced-apart first portions 152 having their first ends 154 pivotally coupled to the foot end 44 of the stretcher 20. The second ends 156 of the laterally spaced-apart first portions 152 are coupled to a pair of laterally spaced-apart second portions 158 extending away from the respective second ends 156 transversely to the first portions. The distal ends of the laterally spaced-apart second portions 158 are coupled to a transversely-extending cross portion 160 by transition portions 166 to form a trough 168 for removably supporting a radiolucent trauma board 200 over the patient support surface 32 in a substantially parallel, spaced-apart relation to the patient support surface 32. The transition portions 166 engage the side edges 204 of the trauma board 200 to securely hold the trauma board 200 in place when supported on the backboard support 150. The first portions 152 extend generally vertically, and the second portions 158 and the cross portion 160 extend generally horizontally over the patient support surface 32 when the trauma board support 150 is in the second position as shown in solid lines in FIG. 5.

In this embodiment, the laterally spaced-apart first portions 152 of the trauma board support 150 include further portions 162 extending away from the respective first ends 154 transversely to the first portions 152 such that the first portions 152, the second portions 158 and the further portions 162 generally form a C-shaped configuration. The distal ends 164 of the further portions 162 are pivotally coupled below the patient support surface 32 to the foot end 44 of the stretcher 20 for motion between a second position above the patient support deck 28 (as shown in solid lines in FIG. 5), and a first position under the foot end 44 of the patient support surface 32 (as shown in phantom lines in FIG. 5). The first portions 152, the second portions 158, the cross portion 160 and the further portions 162 may all be formed by bending a single tubular member into a C-shaped configuration as shown.

In a further alternative embodiment of the present invention also shown in FIG. 5, a headboard 170 is coupled to the head end 42 of the stretcher. A flip-down panel 172 is pivotally coupled to the headboard 170 for movement between a first position (shown in phantom lines in FIG. 5) away from the patient support surface 32, and a second position (shown in solid lines in FIG. 5) above and overlying the patient support surface 32 for removably supporting a trauma board 200 thereon in a substantially parallel, spaced-apart relation to the patient support surface 32 to allow positioning of an x-ray cassette 220 between the trauma board 200 and a mattress 30 supported on the patient support deck 28. In addition to providing support to the trauma board 200 when flipped down, the flip-down panel 172 provides a table surface for use by a patient or a care giver.

It will be recognized that a footboard with a flip-down panel 172 may as well be pivotally coupled to the foot end 44 of the stretcher 20, instead of, to the head end 42 of the stretcher 20. Also, it will be understood that both headboard and footboard may be provided with flip-down panels 172. In addition, flip-down panels 172 may include one or more posts, clamps, latches, etc. to hold the trauma board 200 in place while supported thereon.

Although the invention has been described in detail with reference to certain illustrated embodiments, variations and modifications exist within the scope and spirit of the present invention as described and defined in the following claims.

What is claimed is:

1. A trauma board assembly comprising:

a radiolucent trauma board having a length exceeding the length of a patient for supporting the patient, and a trauma board support mechanism for supporting the radiolucent trauma board relative to a patient support surface of a patient support apparatus, the trauma board support mechanism being configured to be pivotally coupled to the patient support apparatus adjacent to the patient support surface for movement between a first position away from the patient support surface and a second position above the patient support surface, the trauma board support mechanism being adapted to support the trauma board thereon in a spaced-apart relation to the patient support surface to allow positioning of an x-ray cassette between the trauma board and the patient support surface when the trauma board support mechanism is in the second position.

2. The trauma board assembly of claim 1, wherein the trauma board support mechanism includes a portion adapted to be received in a cutout formed in the trauma board for holding the trauma board in place when the trauma board is supported on the trauma board support mechanism.

3. A trauma board assembly comprising:

a radiolucent trauma board having a length exceeding the length of a patient for supporting the patient, and a trauma board support mechanism for supporting the radiolucent trauma board relative to a patient support surface of a patient support apparatus, the trauma board support mechanism being configured to be movably coupled to the patient support apparatus adjacent to the patient support surface for movement between a first position away from the patient support surface and a second position above the patient support surface, the trauma board support mechanism being adapted to support the trauma board thereon in a spaced-apart relation to the patient support surface to allow positioning of an x-ray cassette between the trauma board and the patient support surface when the trauma board support mechanism is in the second position, wherein the trauma board support mechanism includes at least one first portion having a first end adapted to be pivotally coupled to the patient support apparatus generally below the patient support surface and a second end coupled to at least one second portion extending away from the second end transversely to the at least one first portion for removably supporting the trauma board, and wherein the at least one first portion extends generally vertically and the at least one second portion extends generally horizontally over the patient support surface when the trauma board support mechanism is in the second position.

4. The trauma board assembly of claim 3, wherein the trauma board mechanism includes a support socket structure configured to be coupled to the patient support apparatus generally below the patient support surface, wherein the first end of the at least one first portion is configured to be slidably received in the support socket structure, wherein the first end of the at least one first portion includes an elongated pin-receiving slot configured to receive a generally transversely-extending pivot pin secured to the support socket structure, the at least one first portion being configured to be pivoted about the generally transversely-extending pivot pin from a first out-of-the-way down position to a second generally vertical up position and slid downwardly into the support socket structure to lock the at least one first portion in place, the at least one first portion being configured to be lifted upwardly to release the lock and pivoted downwardly to return the at least one first portion to the first out-of-the-way down position.

5. The trauma board assembly of claim 4, wherein the at least one second portion is movable from a first out-of-the-way down position to a second position extending generally horizontally and transversely over the patient support surface in response to movement of the at least one first portion from the first out-of-the-way down position to the second generally vertical up position, wherein the at least one second portion is configured to removably support the trauma board thereon in a spaced-apart relation to the patient support surface to allow positioning of an x-ray cassette between the trauma board and the patient support surface when the at least one second portion is in the second position extending generally horizontally and transversely over the patient support surface, and wherein the at least one second portion of the trauma board support includes a portion configured for engagement with the trauma board for holding the trauma board in place when supported on the at least one second portion.

6. The trauma board assembly of claim 5, wherein the at least one second portion includes a protruding portion configured for reception in a cutout in the trauma board for holding the trauma board in place when supported on the at least one second portion.

7. The trauma board assembly of claim 6, wherein the at least one second portion can telescope in and out along its length dimension to accommodate different width trauma boards.

8. The trauma board assembly of claim 7, wherein the support socket structure is configured to be movable lengthwise along a frame member secured to a side of the patient support apparatus generally below the patient support surface to accommodate different length trauma boards.

9. The trauma board assembly of claim 8, wherein the support socket structure is configured to be moved adjacent to a corner of the patient support apparatus so that the at least one first and second portions can be pivoted down to their respective out-of-the-way down positions generally below the patient support surface.

10. The trauma board assembly of claim 9, wherein the support socket structure comprises two halves configured to form an opening therebetween for slidably receiving the frame member, and wherein the support socket structure includes a thumb screw passing through an oversized opening in one of the two halves thereof for threadably engaging the other of the two halves so that rotation of the thumb screw draws the two halves together to clamp the frame member.

11. A trauma board assembly comprising:

a trauma board having a length exceeding the length of a patient for supporting the patient, and a trauma board support mechanism for supporting the trauma board relative to a patient support surface of a patient support apparatus, the trauma board support mechanism comprising:

at least one first portion adapted to be coupled to the patient-support apparatus generally below the patient support surface, and at least one second portion pivotally coupled to the at least one first portion for movement between a first position and a second position, the at least one second portion being adapted to overlie the patient support surface when the at least one first portion is coupled to the patient-support apparatus and the at least one second portion is in the second position, the at least one second portion being adapted to space the trauma board above the patient support surface.

12. The trauma board assembly of claim 11, wherein the at least one first portion includes a socket structure adapted to be coupled to the patient support apparatus, and the at least one second portion includes an end received in the socket structure when the at least one second portion is in the second position.

13. A trauma board assembly comprising:

a trauma board having a length exceeding the length of a patient for supporting the patient, and a trauma board support mechanism for supporting the trauma board relative to a patient support surface of a patient support apparatus, the trauma board support mechanism comprising:

at least one first portion adapted to be coupled to the patient-support apparatus generally below the patient support surface, and at least one second portion coupled to the at least one first portion for movement between a first position and a second position, the at least one second portion being adapted to overlie the patient support surface when the at least one first portion is coupled to the patient-support apparatus and the at least one second portion is in the second position, the at least one second portion being adapted to space the trauma board above the patient support surface, wherein the at least one first portion includes a socket structure adapted to be coupled to the patient support apparatus, wherein the at least one second portion includes an end received in the socket structure when the at least one second portion is in the second position, and wherein the at least one second portion is L-shaped having a first generally vertically-extending section pivotally coupled to the socket structure and a second generally horizontally-extending section that overlies the patient support surface when the at least one second portion is in the second position.

14. The trauma board assembly of claim 13, wherein the second generally horizontally-extending section includes a retainer adapted to be received in a cutout of the trauma board to hold the trauma board in place when supported on the second generally horizontally-extending section.

15. The trauma board assembly of claim 14, wherein the second generally horizontally-extending section includes a tubular portion and a rod coupled to the tubular portion for telescoping movements.

16. A trauma board support mechanism for supporting a trauma board relative to a longitudinally-extending patient support surface, the trauma board support mechanism comprising:

a support socket structure configured to be coupled generally below the patient support surface, at least one first portion having a first end configured to be slidably received in the support socket structure, the first end of the at least one first portion including an elongated pin-receiving slot configured to receive a generally transversely-extending pivot pin secured to the support socket structure, the at least one first portion being configured to be pivoted about the generally transversely-extending pivot pin from a first out-of-the-way down position to a second generally vertical up position and slid downwardly into the support socket structure to lock the at least one first portion in place, the at least one first portion being configured to be lifted upwardly to release the lock and pivoted downwardly to return the at least one first portion to the first out-of-the-way down position, and at least one second portion extending transversely from a second end of the at least one first portion, the at least one second portion being movable from a first out-of-the-way down position to a second position extending generally horizontally and transversely over the patient support surface in response to movement of the at least one first portion from the first out-of-the-way down position to the second generally vertical up position, the at least one second portion being configured to removably support the trauma board thereon in a spaced-apart relation to the patient support surface to allow positioning of an x-ray cassette between the trauma board and the patient support surface when the at least one second portion is in the second position extending generally horizontally and transversely over the patient support surface.

* * * * *